(12) United States Patent
Fröjd

(10) Patent No.: US 9,649,471 B2
(45) Date of Patent: *May 16, 2017

(54) CATHETER ASSEMBLY WITH RESEALABLE OPENING

(71) Applicant: ASTRA TECH AB, Mölndal (SE)

(72) Inventor: Göran Fröjd, Göteborg (SE)

(73) Assignee: ASTRA TECH AB, Molndal (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/910,675

(22) Filed: Jun. 5, 2013

(65) Prior Publication Data

US 2013/0264227 A1  Oct. 10, 2013

Related U.S. Application Data

(63) Continuation of application No. 12/875,179, filed on Sep. 3, 2010, now Pat. No. 8,459,455.

(60) Provisional application No. 61/240,084, filed on Sep. 4, 2009.

(30) Foreign Application Priority Data

Sep. 4, 2009 (EP) ..................... 09169522

(51) Int. Cl.
*A61M 25/00* (2006.01)
*B65B 5/04* (2006.01)

(52) U.S. Cl.
CPC ............. *A61M 25/002* (2013.01); *B65B 5/04* (2013.01); *A61M 25/0017* (2013.01); *A61M 2025/0046* (2013.01)

(58) Field of Classification Search
CPC ........ A61M 25/002; A61M 2025/0046; A61M 25/0017; B65D 72/58; B65D 2101/00; B65B 11/50; A61B 50/30
USPC ....... 206/364, 210, 571, 438, 205, 570, 363, 206/370, 484, 809; 383/5; 604/544
See application file for complete search history.

(56) References Cited

U.S. PATENT DOCUMENTS

| 2,947,415 A | 8/1960 | Garth |
| 3,761,013 A | 9/1973 | Schuster |
| 3,967,728 A | 7/1976 | Gordon et al. |

(Continued)

FOREIGN PATENT DOCUMENTS

| EP | 0 217 771 A1 | 4/1987 |
| GB | 1 280 362 | 7/1972 |

(Continued)

*Primary Examiner* — Steven A. Reynolds
(74) *Attorney, Agent, or Firm* — Birch, Stewart, Kolasch & Birch, LLP

(57) ABSTRACT

A catheter assembly includes a catheter, preferably having a hydrophilic surface coating; and a package accommodating said catheter. The package preferably also accommodates a wetting fluid. The package includes a first and a second sheet material connected around the edges; a perforation line extending along a non-closed loop in one of said sheet materials, which defines a flap opening; a third sheet material connected by means of an adhesive over said flap opening. The third sheet material with a margin covers the entire flap opening. The adhesive is adapted to maintain a sterile closure of the package before use, and to be resealable after use. The third sheet material forms a tab not provided with adhesive and the tab provides a grip portion for peel opening of the package.

29 Claims, 3 Drawing Sheets

(56) References Cited

U.S. PATENT DOCUMENTS

| | | | |
|---|---|---|---|
| 4,552,269 A | 11/1985 | Chang | |
| 5,895,374 A | 4/1999 | Rodsten | |
| 6,065,597 A | 5/2000 | Pettersson et al. | |
| 6,364,112 B1 * | 4/2002 | Pitschka | 206/460 |
| 6,589,622 B1 | 7/2003 | Scott | |
| 6,889,483 B2 | 5/2005 | Compton et al. | |
| 7,476,223 B2 | 1/2009 | McBride | |
| 7,615,045 B2 | 11/2009 | Israelsson et al. | |
| 7,770,726 B2 | 8/2010 | Murray et al. | |
| 2003/0168365 A1 | 9/2003 | Kaern | |
| 2004/0083680 A1 | 5/2004 | Compton et al. | |
| 2005/0109648 A1 | 5/2005 | Kerzman et al. | |
| 2006/0171611 A1 * | 8/2006 | Rapparini | 383/66 |
| 2006/0289336 A1 | 12/2006 | Ford et al. | |
| 2007/0275133 A1 | 11/2007 | Sierra-Gomez et al. | |
| 2009/0208368 A1 | 8/2009 | Waldrep et al. | |
| 2009/0226117 A1 * | 9/2009 | Davis et al. | 383/5 |

FOREIGN PATENT DOCUMENTS

| | | |
|---|---|---|
| JP | 60-179606 A | 9/1985 |
| JP | 2001-500414 A | 1/2001 |
| WO | WO 98/11932 A1 | 3/1998 |
| WO | WO 2005/067863 A1 | 7/2005 |

* cited by examiner

CATHETER ASSEMBLY WITH RESEALABLE OPENING

CROSS-REFERENCE TO RELATED APPLICATIONS

This application is a Continuation of U.S. application Ser. No. 12/875,179 filed on Sep. 3, 2010, which claims the benefit under 35 U.S.C. §119(e) of U.S. Provisional Application No. 61/240,084 filed on Sep. 4, 2009 and under 35 U.S.C. 119(a) to patent application Ser. No. 09/169,522.1 filed in Europe on Sep. 4, 2009. The entire contents of all of the above applications are hereby incorporated by reference into the present application.

TECHNICAL FIELD OF THE INVENTION

The present invention relates to a catheter assembly comprising a catheter and a resealable package accommodating the catheter. Specifically, the invention pertains to a catheter having a hydrophilic surface coating, wherein the assembly also includes a wetting fluid for activation of the hydrophilic surface coating. The invention is particularly related to urinary catheters.

BACKGROUND

The present invention relates to a catheter assembly for hydrophilic catheters. Catheters are commonly used for draining bodily fluids, e.g. from the bladder. Urinary catheters are e.g. used by a large group of persons for intermittent catheterization, which is a daily-life procedure, taking place several times a day. Typically catheters for intermittent catheterization are used by patients suffering from urinary incontinence or by disabled individuals like para- or tetraplegics. Using an intermittent catheter, the bladder may be drained through a natural or artificial urinary canal. Many catheters for intermittent catheterization are provided with a hydrophilic coating or the like, providing a smooth and slippery surface when wetted, for safe and comfortable insertion in the urinary canal.

Many hydrophilic catheter assemblies include a supply of wetting fluid, either in direct contact with the catheter or in a separate compartment, for clean and convenient activation of the hydrophilic surface before use.

However, there is still a need for improved packages for such catheter assemblies. The package should preferably be relatively simple and cost-efficient to produce. Further, the package should be easy to open, even for users with reduced dexterity. Still further, the package should enable adequate wetting of the catheter, and handling of the package in a clean manner. The package should also preferably be rather small, so that it can easily be carried around by the user in his/hers daily life. It would also be highly advantageous if the package is resealable, so that the catheter could be re-closed after use, if it cannot be immediately disposed of. In particular, it would be advantageous if the package would be resealable to enclose also a wet product and/or a wetting fluid without any risk for spillage.

In conclusion there is still a need for an improved catheter assembly of the above discussed general type.

SUMMARY OF THE INVENTION

It is therefore an object of the present invention to provide a catheter assembly which at least alleviates the above-discussed problems.

This object is obtained by means of a catheter assembly in accordance with the appended claims.

According to the present invention there is provided a catheter assembly comprising:
 a catheter, preferably having a hydrophilic surface coating; and
 a package accommodating said catheter;
 wherein said package comprises:
 a first and a second sheet material connected around the edges;
 a perforation line extending along a non-closed loop in one of said sheet materials, said perforation line defining a flap opening;
 a third sheet material connected by means of an adhesive over said flap opening, wherein said third sheet material with a margin covers the entire flap opening
 wherein said adhesive is adapted to maintain a sterile closure of the package before use, and to be resealable after use; and
 wherein said third sheet material further forms a tab not provided with adhesive, said tab providing a grip portion for peel opening of the package.

In the context of the present application, "perforation line" is used to indicate a line forming a weakening, such as a total cut-through, a partial cut-through, point perforations, or the like, forming a weakening where a rupture will occur when a force is exerted on the material.

In the context of the present application, "resealing" relates to closure of a previously opened opening, wherein the closure forms closure that at least to a large extent prevents liquid from leaking out from the closure.

By "perforation" is meant a diminished material thickness, possibly extending over the entire thickness, providing a complete cut-through. By means of "perforation line" is meant a line with continuous or discontinuous perforations.

This package is very well suited for use for hydrophilic catheters. The package enables easy, clean and efficient wetting and handling of the hydrophilic catheter. At the same time the package is relatively simple and cost-efficient to produce. In particular, the catheter assembly is well-suited for the type of assemblies including a hydrophilic catheter and a wetting fluid being accommodated by the package. The wetting fluid may e.g. be arranged directly in contact with the hydrophilic surface of the catheter, or in a separate compartment of the package or in a separate container being housed by the package.

However, even though the catheter assembly is at present primarily intended for urinary hydrophilic catheters, where the package also includes a wetting fluid, the catheter assembly may also be used for other types of catheters. For example, the catheter may be other types of catheters, such as vein catheters and the like. Further, the catheter may be provided with other types of lubricious coatings, such as gel lubricants and the like, or being without any surface coating at all. Still further, assemblies without a wetting fluid are also feasible.

The tab enables a very simple peel-opening of the package. At the same time, the flap opening provides an efficient for removal of the catheter, and also for resealing of the package, once the catheter has been used and been replaced in the package.

In production, one of the first and second sheets may be provided with the non-closed loop perforation line, by means of cutting or the like, and the third sheet material can thereafter be adhered on top of it.

Preferably a wetting fluid is also included in the assembly. The wetting fluid may be arranged in direct contact with the hydrophilic surface of the catheter. However, preferably the wetting fluid is arranged separately from said catheter within the package. The separate arrangement of the wetting fluid can be obtained by means of closed compartment within the package. However, in a preferred embodiment, the wetting fluid is arranged in a wetting fluid container arranged within said package, such as in a pouch, sachet or the like. In case the wetting fluid is arranged separately, the container or compartment is openable into the part of the package housing the catheter, in order to enable release of the wetting fluid into contact with the hydrophilic part of the catheter before use. Release of the wetting fluid can be obtained by squeezing, bending or the like, as is per se well known in the art.

The catheter preferably comprises an insertion end and a connector end, wherein the flap opening is arranged overlying the connector end of said catheter. Hereby, the catheter may be withdrawn with the connector end first, which enables a clean and convenient way of handling the catheter without touching the insertable part directly by hand.

The non-closed loop defining the flap opening preferably debouches towards (i.e. faces) the end of the package being opposite to the insertion end of the catheter. Hereby, the tab is arranged close to the middle of the package, and the peeling occurs upwards, towards the end, which is efficient for avoiding spillage of the wetting fluid within the package after activation.

The third sheet material preferably covers the entire flap opening with a margin exceeding 2 mm, and preferably exceeding 5 mm. Hereby, a sterile seal may be obtained before opening of the package, and at the same time an adequate resealing capability may be obtained.

Preferably, the non-closed loop of the perforation line forms a tongue directed inwardly towards the non-closed opening of the non-closed loop. Hereby, an opening is provided making re-insertion of the catheter into the package very easy, since e.g. sticking of the package material around the opening to the underlying sheet is avoided.

Further, the non-closed loop preferably has loop ends directed towards the interior of the non-closed loop. Hereby, it is efficiently avoided that the third material sheet is peeled off completely.

The third sheet material may further comprise a weakened area forming a seal integrity mark. Hereby, it is ensured that the seal has not been broken before use, ensuring full integrity of the product. Preferably, the seal integrity mark is arranged between the tab and the part of the third sheet material overlying the perforation line.

The catheter assembly may further comprise a fourth sheet material arranged on the side of said package being opposed to the third sheet material, wherein the fourth sheet material is connected by means of an adhesive to said package, and forming a tab not provided with adhesive, said tab providing a grip portion for exposure of said adhesive to form a holding arrangement for said package. By means of this fourth sheet material, the catheter assembly may e.g. be attached to a sink, a wall or the like, which enables very efficient and easy handling of the product, even for user with reduced dexterity.

The first and second sheet materials are preferably connected around the edges by means of welding. Preferably, the first and second sheet materials comprise laminated sheets, having a weldable inner layer and a protective outer layer.

In a preferred embodiment, the package is elongate, and preferably with an essentially rectangular form. Hereby, a very compact product is obtained. It is further preferred that the short side of the elongate package being closest to the flap opening has an inwardly protruding shape. Hereby wrinkling, buckling and the like of the package are avoided, ensuring a tight seal by means of the third sheet material.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DETAILED DESCRIPTION OF PREFERRED EMBODIMENTS

Figure 1:
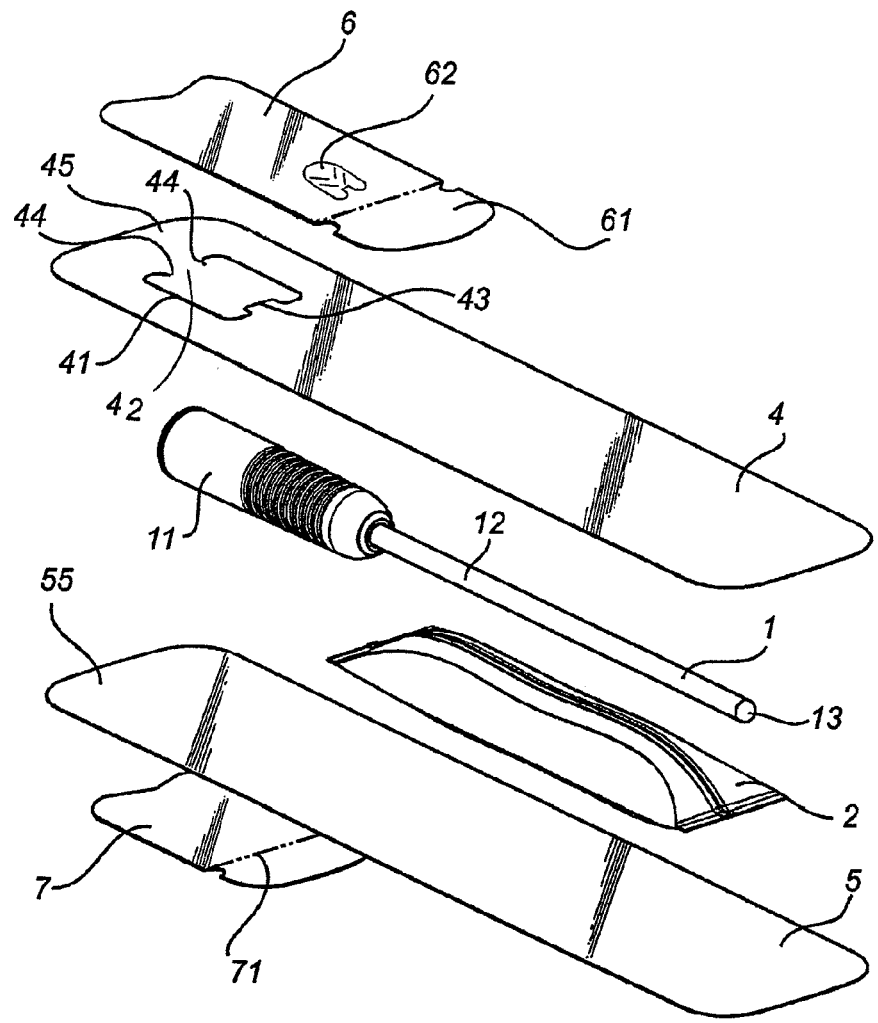
FIG. 1 illustrates an exploded view of a catheter assembly in accordance with an embodiment of the present invention.

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g. the length of the catheter, etc.

Catheters may be used for many different purposes, and for insertion into various types of body-cavities. However, the following discussion is in particular concerned with the preferred field of use, hydrophilic urinary catheters, even though the invention is not limited to this particular type of catheters.

Figure 2:
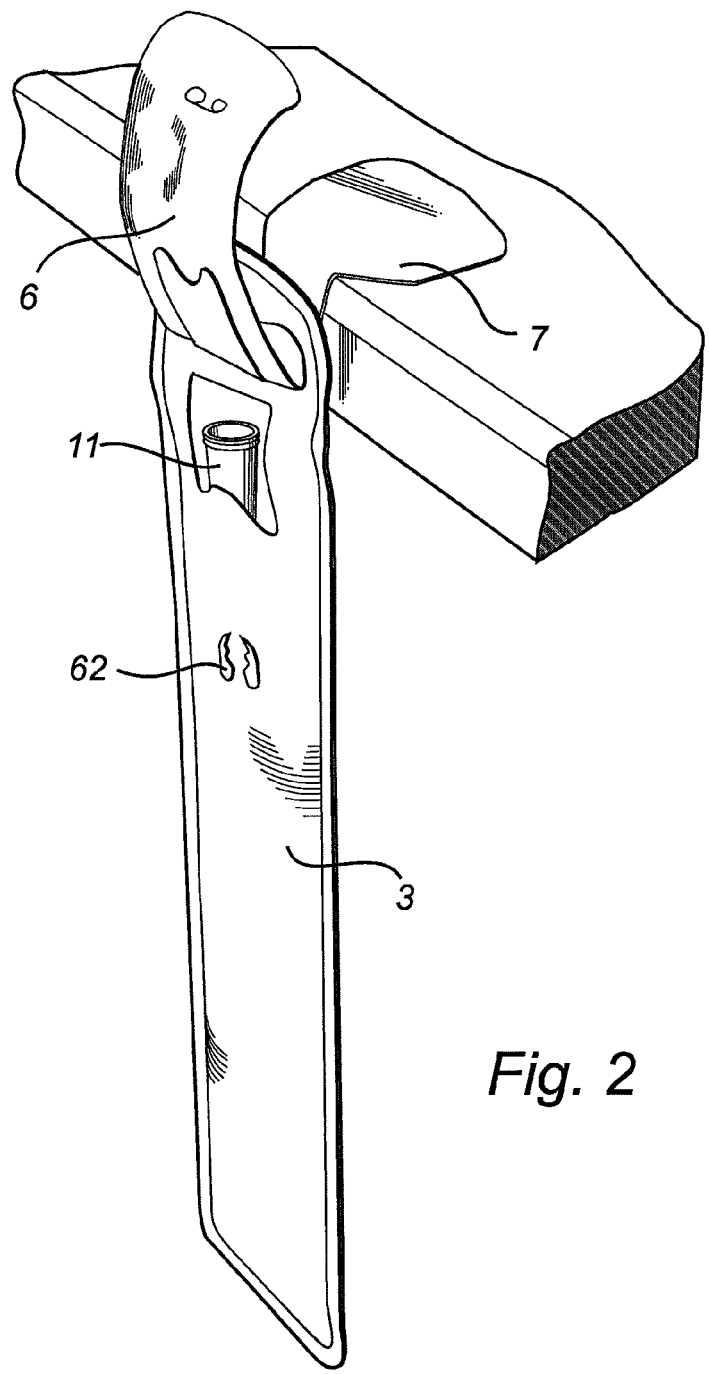
FIG. 2 illustrates the assembly in FIG. 1 in a use condition.
Figure 3:
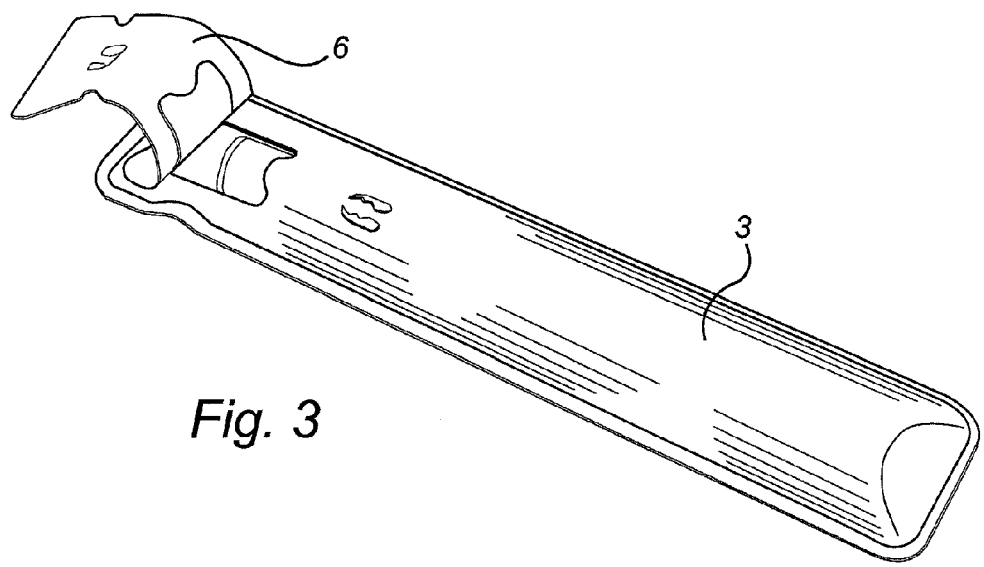
FIG. 3 illustrates the assembly in FIG. 1 in another use condition.

The catheter assembly as illustrated in FIGS. 1-3 comprises a catheter 1 having a hydrophilic surface coating, a wetting fluid for activation of said hydrophilic surface coating and a package 3 accommodating the catheter and the wetting fluid.

The catheter 1 may be any type of hydrophilic catheter, as is per se well known in the art. Preferably, the catheter comprises a flared rearward portion, forming a flared connector 11, and an elongated shaft 12, connected to the flared connector 11, and in the opposite end having a catheter insertion end 13.

At least a part of the elongate shaft 12 forms an insertable length to be inserted through a body opening of the user, such as the urethra in case of a urinary catheter. By insertable length is normally, in the context of a hydrophilic catheter, meant that length of the elongate shaft 12 which is coated with a hydrophilic material, for example PVP, and which is insertable into the urethra of the patient. Typically, this will be 50-140 mm for a female patient and 200-350 mm for a male patient. Even though PVP is the preferred hydrophilic material, other hydrophilic materials may be used, such as hydrophilic polymers selected from polyvinyl compounds, polysaccharides, polyurethanes, polyacrylates or copolymers of vinyl compounds and acrylates or anhydrides, especially polyethyleneoxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anhydride. The coating may also comprise an osmolality-increasing compound, as is e.g. taught in EP 0 217 771.

The wetting fluid is preferably arranged separate from the catheter, in a wetting fluid container 2, such as a pouch or a sachet. The wetting fluid container is openable by means of e.g. exerting a pressure to the container, whereby the wetting fluid is released into the package, thereby wetting the hydrophilic surface of the catheter. The wetting fluid is preferably an aqueous liquid, such as water or saline. Such wetting fluid containers and wetting fluids are per se well known in the art. The wetting fluid container can e.g. be made of sheet material comprising aluminium.

The wetting fluid may be any fluid that wets a hydrophilic surface of the catheter.

Preferably, the wetting fluid container 2 is arranged close to the insertion end of the catheter, whereby a compact catheter assembly can be obtained.

The package comprises a first sheet material 4 and a second sheet material 5, connected around the edges to form an inner cavity housing the catheter and the wetting fluid. The first and second sheet materials are preferably connected around the edges by means of welding. Preferably, the first and second sheet materials comprise laminated sheets, having a weldable inner layer and a protective outer layer.

The first sheet material comprises a perforation line 41 extending along a non-closed loop defining a flap opening. The non-closed loop defining the flap opening is preferably arranged over the connector end of the catheter 1. Further, the non-closed loop preferably has an opening 42 debouching towards the end of the package being opposite to the insertion end of the catheter. At the other end, the non-closed loop preferably forms a tongue 43 directed inwardly towards the non-closed opening of the non-closed loop. The loop ends, at the opening 42, are preferably directed towards the interior of the non-closed loop.

The non-closed loop generally forms a C- or U-shape.

Over the non-closed loop, a third sheet material 6 is arranged, and connected to the first sheet material 4 by means of an adhesive. The third sheet material is arranged to cover the entire flap opening with a margin, preferably exceeding 2 mm, and most preferably exceeding 5 mm. An end of the third sheet material is not adhered to the first sheet material, and forms a tab 61 providing a grip portion for peel opening of the package. The tab is preferably arranged in the end directed towards the insertable part of the catheter.

In the tab 61, close to the part of the third sheet material adhered to the first sheet material, there can be provided indentation(s), at least on one side and preferably on both sides. The indentation(s) form(s) a waist in the third sheet material. This waist reduces the tendency of the tab to stick to the material and enhances the flatness of the tab. Hereby, gripping of the tab becomes easier.

The adhesive is adapted to maintain a sterile closure of the package before use, and to be resealable after use. The adhesive preferably has a strength to withstand a pulling force in the range of 3-10 N. The adhesive can e.g. be an acrylate emulsion, or an acrylate based hot melt adhesive.

The third sheet material further preferably comprises a weakened area 62 forming a seal integrity mark. Hereby, it is ensured that the seal has not been broken before use, ensuring full integrity of the product. Preferably, the seal integrity mark is arranged between the tab and the part of the third sheet material overlying the perforation line. The weakened area preferably comprises weakened or perforated lines arranged in a pattern, e.g. as illustrated in the drawings, making part of the third sheet material to remain adhered to the first sheet material during peel off of the third sheet material.

The catheter assembly may further comprise a fourth sheet material 7 arranged on the second sheet material, i.e. on the side of the package being opposed to the third sheet material. The fourth sheet material is also connected by means of an adhesive to the package, and forms a tab 71 not provided with adhesive, said tab providing a grip portion for exposure of said adhesive to form a holding arrangement for the package. By means of this fourth sheet material, the catheter assembly may e.g. be attached to a sink, a wall or the like, which enables very efficient and easy handling of the product, even for user with reduced dexterity.

In the tab 71, close to the part of the fourth sheet material adhered to the second sheet material, there may also be provided indentation(s), at least on one side and preferably on both sides. The indentation(s) form(s) a waist in the fourth sheet material. This waist reduces the tendency of the tab to stick to the material and enhances the flatness of the tab. Hereby, gripping of the tab becomes easier.

In order to ensure that the fourth sheet materials are not removed completely during peeling, perforated lines 72 may be arranged on one or preferably both of the sides. The perforated lines preferably extend from the outer side of the fourth sheet material, about in the center of the sheet material, towards the interior of the sheet in a direction away from the pulling tab. The tear line preferably ends in a hook or the like towards the side of the sheet, but not extending entirely to the side of the sheet.

The third and fourth sheet materials may e.g. be of polypropene (polypropylene), polyester or polyethen (polyethylene).

In a preferred embodiment, the package is elongate, and preferably with an essentially rectangular form. Hereby, a very compact product is obtained. It is further preferred that the short side 45, 55 of the elongate package being closest to the flap opening has an inwardly protruding shape. Hereby wrinkling, buckling and the like of the package is avoided, ensuring a tight seal by means of the third sheet material.

In use, the wetting fluid container is opened, for activation of the hydrophilic surface of the catheter. After sufficient wetting, the tab of the fourth sheet may be peeled, so that the catheter assembly can be connected to a sink or the like (see FIG. 2). The tab of the third sheet is peeled open, and the catheter is removed and used. Thereafter, the catheter may be re-inserted, (see FIG. 3), and the package can then be closed, and stored for later disposal.

A method of manufacturing the above-discussed catheter assembly preferably comprises the following steps of producing the package, performed in any order:
Providing a first and second sheet material;
Providing the non-closed loop perforated line in the first sheet material by cutting the material;
Connecting the first and second sheet material to each other along the edges by means of welding;
Providing third sheet materials;
Providing the perforated lines in the third sheet material;
Adhering the third sheet material to the first sheet material;
Providing the fourth sheet material;
Providing the perforated lines in the fourth sheet material; and Adhering the fourth sheet material to the second sheet material.

In addition, the catheters and the wetting fluid container is provided and arranged within the package before the package is finally closed, and sterilization of the product is provided by means of e.g. radiation.

Figure 4:
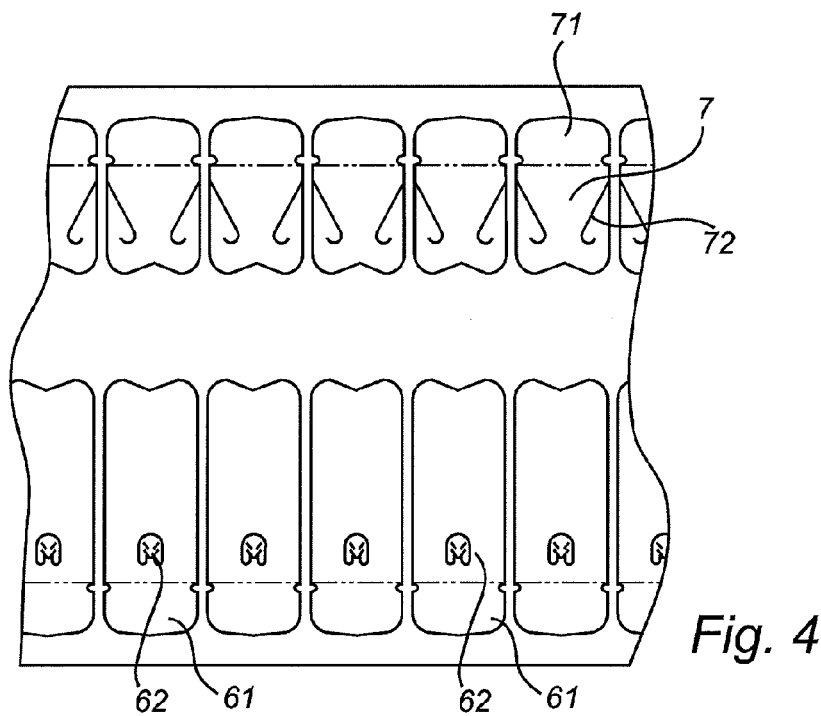
FIG. 4 illustrates third and fourth sheet materials arranged on a production sheet.

The third and fourth sheet material may be provided on large sheets, arranged on a layer of adhesive, and with the perforation lines pre-arranged before assembly. Such a sheet is illustrated in FIG. 4.

The invention has now been described by means of preferred embodiments. However, many further variations are possible. For example, a package without the fourth sheet is feasible, and other sheets may also be used. Further, other shapes for the various perforation lines are feasible. Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A catheter assembly comprising:
   a catheter having a hydrophilic surface coating; and
   a package accommodating said catheter;
   wherein said package is formed of sheet material and comprises:
      a perforation line extending along a non-closed loop in said sheet material, said perforation line defining a flap opening, wherein the non-closed loop has loop ends directed towards the interior of the non-closed loop;
      an additional sheet material connected by means of an adhesive over said flap opening, wherein said additional sheet material with a margin covers the entire flap opening,
   wherein said adhesive is adapted to maintain a sterile closure of the package before use, and to be resealable after use; and
   wherein said additional sheet material further forms a tab not provided with adhesive, said tab providing a grip portion for peel opening of the package.

2. The catheter assembly of claim 1, wherein the assembly further comprises a wetting fluid for activation of said hydrophilic surface coating, said wetting fluid being accommodated by said package.

3. The catheter assembly of claim 2, wherein the wetting fluid is arranged separately from said catheter in said package.

4. The catheter assembly of claim 3, wherein the catheter comprises an insertion end and a connector end, wherein the flap opening is arranged overlying the connector end of said catheter.

5. The catheter assembly of claim 3, wherein the additional sheet material covers the entire flap opening with a margin exceeding 2 mm.

6. The catheter assembly of claim 2, wherein the catheter comprises an insertion end and a connector end, wherein the flap opening is arranged overlying the connector end of said catheter.

7. The catheter assembly of claim 2, wherein the additional sheet material covers the entire flap opening with a margin exceeding 2 mm.

8. The catheter assembly of claim 2, wherein the wetting fluid is arranged in a wetting fluid container arranged within said package.

9. The catheter assembly of claim 2, wherein the additional sheet material covers the entire flap opening with a margin exceeding 5 mm.

10. The catheter assembly of claim 1, wherein the additional sheet material covers the entire flap opening with a margin exceeding 2 mm.

11. The catheter assembly of claim 1, wherein the non-closed loop of the perforation line forms a tongue directed inwardly towards a non-closed opening of the non-closed loop.

12. The catheter assembly of claim 1, wherein the additional sheet material further comprises a weakened area forming a seal integrity mark.

13. The catheter assembly of claim 12, wherein the seal integrity mark is arranged between the tab and the part of the additional sheet material overlying the perforation line.

14. The catheter assembly of claim 12, wherein the weakened area forming the seal integrity mark is arranged fully within the bounds of the part of the additional sheet being adhered to the sheet material of the package so that the weakened area is fully encircled by parts of the additional sheet not forming said weakened area.

15. The catheter assembly of claim 1, further comprising an opposite sheet material arranged on the side of said package being opposed to the additional sheet material, said opposite sheet material being connected by means of an adhesive to said package, and forming a tab not provided with adhesive, said tab providing a grip portion for exposure of said adhesive to form a holding arrangement for said package.

16. The catheter assembly of claim 1, wherein the sheet material of the package forms connections around the edges by means of welding.

17. The catheter assembly of claim 1, wherein the sheet material of the package comprises laminated sheets, having a weldable inner layer and a protective outer layer.

18. The catheter assembly of claim 1, wherein the package is elongate.

19. The catheter assembly of claim 1, wherein the additional sheet material covers the entire flap opening with a margin exceeding 5 mm.

20. The catheter assembly of claim 1, wherein the package is elongate with an essentially rectangular form.

21. The catheter assembly of claim 1, wherein the adhesive has a strength to withstand a pulling force in the range of 3-10 N.

22. The catheter assembly of claim 1, wherein the additional sheet material is made of a material being selected from the group consisting of polypropene (polypropylene), polyester and polyethen (polyethylene).

23. The catheter assembly of claim 1, wherein the additional sheet material is comprised of an adhered part that is adhered to the sheet material of the package and the tab, the tab being formed as a free end, and an indentation is provided on at least one side of the tab at a location adjacent to the adhered part.

24. The catheter assembly of claim 23, wherein the indentation is provided on each side of the tab at a location adjacent to the adhered part.

25. A catheter assembly comprising:
a catheter having a hydrophilic surface coating, the catheter comprising an insertion end and a connector end; and
a package accommodating said catheter,
wherein said package is formed of sheet material and comprises:
a perforation line extending along a non-closed loop in said sheet materials, said perforation line defining a flap opening, wherein the non-closed loop defining the flap opening debouches towards the end of the package being opposite to the insertion end of the catheter;
an additional sheet material connected by means of an adhesive over said flap opening, wherein said additional sheet material with a margin covers the entire flap opening,
wherein said adhesive is adapted to maintain a sterile closure of the package before use, and to be resealable after use, and
wherein said additional sheet material further forms a tab not provided with adhesive, said tab providing a grip portion for peel opening of the package.

26. A method of producing a catheter assembly comprising the steps:
providing a catheter having a hydrophilic surface coating, the catheter comprising an insertion end; and a connector end;
accommodating the catheter in a package of a sheet material, said package comprising:
a perforation line extending along a non-closed loop in said sheet material, said perforation line defining a flap opening, wherein the non-closed loop has loop ends directed towards the interior of the non-closed loop; and;
providing an additional sheet material connected by means of an adhesive over said flap opening, wherein said additional sheet material with a margin covers the entire flap opening,
wherein said adhesive is adapted to maintain a sterile closure of the package before use, and to be resealable after use; and
wherein said additional sheet material further forms a tab not provided with adhesive, said tab providing a grip portion for peel opening of the package.

27. A urinary catheter assembly comprising:
a urinary catheter having a hydrophilic surface coating;
a package accommodating said catheter, and being arranged to maintain a sterile closure of the package before use;
a wetting fluid for activation of said hydrophilic surface coating, said wetting fluid being accommodated by said package;
wherein said package comprises a perforation line defining an opening in a sheet material of said package, wherein the non-closed loop has loop ends directed towards the interior of the non-closed loop;
a further sheet material connected by means of an adhesive over said opening, wherein said further sheet material with a margin covers the entire opening,
wherein said adhesive is adapted to maintain a sterile closure of the package before use, and to be resealable after use; and
wherein said further sheet material further forms a tab not provided with adhesive, said tab providing a grip portion for peel opening of the package.

28. A catheter assembly comprising:
a catheter having an insertion end and an opposite, non-insertable end; and
a package accommodating said catheter, the package being made of a sheet material and being arranged to maintain a sterile closure of the package before use;
wherein said package comprises a perforation line extending along a non-closed loop in the sheet material, said perforation line defining a flap opening arranged overlying the non-insertable end, the non-closed loop debouching towards the end of the package being opposite to the insertion end of the catheter; and
an additional sheet material connected by means of an adhesive over said flap opening and with a margin covering the entire flap opening, the adhesive being adapted to maintain a sterile closure of the package before use, and to be resealable after use, wherein said additional sheet material further forms a tab providing a grip portion for peel opening of the package.

29. A catheter assembly comprising:
a catheter comprising an insertion end;
a package accommodating said catheter, the package being made of a sheet material and being arranged to maintain a sterile closure of the package before use;
wherein said package comprises a perforation line extending along a non-closed loop in the sheet material, said perforation line defining a flap opening, and wherein the non-closed loop has loop ends directed towards the interior of the non-closed loop; and
an additional sheet material connected by means of an adhesive over said flap opening and with a margin covering the entire flap opening, the adhesive being adapted to maintain a sterile closure of the package before use, and to be resealable after use, wherein said additional sheet material further forms a tab providing a grip portion for peel opening of the package.

* * * * *